United States Patent
Ishibashi et al.

(10) Patent No.: US 9,551,683 B2
(45) Date of Patent: Jan. 24, 2017

(54) CONTROLLED POTENTIAL ELECTROLYSIS GAS SENSOR

(71) Applicant: NEW COSMOS ELECTRIC CO., LTD., Osaka (JP)

(72) Inventors: Kenji Ishibashi, Osaka (JP); Toru Maekawa, Osaka (JP); Chise Minagoshi, Osaka (JP); Teppei Takagi, Osaka (JP)

(73) Assignee: NEW COSMOS ELECTRIC CO., LTD., Osaka (JP)

( * ) Notice: Subject to any disclaimer, the term of this patent is extended or adjusted under 35 U.S.C. 154(b) by 0 days.

(21) Appl. No.: 14/895,435

(22) PCT Filed: Jun. 18, 2014

(86) PCT No.: PCT/JP2014/066188
§ 371 (c)(1),
(2) Date: Dec. 2, 2015

(87) PCT Pub. No.: WO2014/203939
PCT Pub. Date: Dec. 24, 2014

(65) Prior Publication Data
US 2016/0103091 A1    Apr. 14, 2016

(30) Foreign Application Priority Data
Jun. 18, 2013 (JP) ................. 2013-127649

(51) Int. Cl.
*G01N 27/404* (2006.01)
*G01N 27/30* (2006.01)

(52) U.S. Cl.
CPC ............ *G01N 27/404* (2013.01); *G01N 27/30* (2013.01)

(58) Field of Classification Search
CPC ... G01N 27/404; G01N 27/4045; G01N 27/30
See application file for complete search history.

(56) References Cited

FOREIGN PATENT DOCUMENTS

| JP | 2004093144 A | 3/2004 |
|---|---|---|
| JP | 2007240437 A | 9/2007 |

OTHER PUBLICATIONS

International Preliminary Report on Patentability dated Dec. 22, 2015 from corresponding Japanese PCT International Application No. PCT/JP2014/066188, 4 pages.
International Search Report and Written Opinion of the International Searching Authority dated Sep. 9, 2014 from corresponding Japanese PCT International Application No. PCT/JP2014/066188, 5 pages.

*Primary Examiner* — J. Christopher Ball
(74) *Attorney, Agent, or Firm* — Innovation Capital Law Group, LLP; Vic Lin (57) ABSTRACT

A controlled potential electrolysis gas sensor including, as gas electrodes 10 for detecting gas, a working electrode for electrochemically reacting gas to be detected, a counter electrode with respect to the working electrode, and a reference electrode for controlling potential of the working electrode, the gas electrodes 10 being disposed to face an electrolysis solution accommodating portion of an electrolysis tank accommodating electrolytic solution 20. Each electrode 10 includes a noble metal catalyst layer 50. On the noble metal catalyst layer 50 of at least one of the working electrode and the reference electrode, there is formed a polymer layer 60 having ion conductivity and water permeability.

4 Claims, 8 Drawing Sheets

Fig.9D ic solution.

CONTROLLED POTENTIAL ELECTROLYSIS GAS SENSOR

TECHNICAL FIELD

The present invention relates to a controlled potential electrolysis gas sensor including, as gas electrodes for detecting gas, a working electrode for electrochemically reacting gas to be detected, a counter electrode with respect to the working electrode, and a reference electrode for controlling potential of the working electrode, the gas electrodes being disposed to face an electrolysis solution accommodating portion of an electrolysis tank accommodating electrolytic solution.

BACKGROUND ART

In a conventional controlled potential electrolysis gas sensor, its electrodes are disposed to face the interior of an electrolysis solution accommodating portion of an electrolysis solution tank that holds electrolysis solution in a sealing manner; and as the electrodes, there are provided e.g. three electrodes consisting of a working electrode for electrochemically reacting gas to be detected, a counter electrode with respect to the working electrode, and a reference electrode for controlling potential of the working electrode. And, there are connected the electrolysis tank holding electrolysis solution to which the electrodes can contact, a potentiostat circuit or the like for setting potentials of the respective electrodes. As materials for forming the three electrodes above, a noble metal catalysis of platinum, gold or palladium or the like is applied to a gas-permeable, porous PTFE membrane having water repellant property was employed and as electrolysis solution, acidic water solution of sulfuric acid, phosphoric acid or the like was employed.

Further, the controlled potential electrolysis gas sensor is configured to generate, between the working electrode and the counter electrode, a current corresponding to an environmental change in the surrounding by controlling potential of the working electrode relative to such environmental change in the surrounding to maintain it constant. Further, with utilization of the potential of the working electrode being maintained constant and an oxidization reduction potential varying according to gas species, according to potential set by the potentiostat circuit, selective detection of gas is made possible. Also, by changing the catalyst to be used for the gas electrode, it is possible to provide high selectivity for a target gas.

As a noble gas catalyst to be applied to an electrode, it was known to employ one having gold particles in the order of several hundreds nm supported to carbon having a particle size of few tens of nm, for instance. In order to cause carbon to support gold particles as described above, the immersion supporting technique is sometimes employed. When noble metal particles are to be supported to a support by this immersion supporting technique, this support is immersed in a water solution of metal salt for allowing metal component to be adsorbed to the surface of the support. Then, drying, sintering and reduction are carried out. After fabrication of gold supported carbon by the above immersion supporting technique, this would be applied to a porous PTFE membrane, thus forming an electrode.

Incidentally, the above-described controlled potential electrolysis gas sensor constituting a conventional art for the present invention is a standard technique, so no particular prior-art documents relevant thereto such as patent documents will be cited herein.

SUMMARY

Problem to be Solved by Invention

The electrode reaction in the above-described controlled potential electrolysis gas sensor takes place at the so-called three-phase interface of an electron conductor (electrode), an ion conductor (electrolysis solution) and reaction gas. And, this three-phase interface is present in the vicinity of the surface of noble metal catalysis applied to the electrode. In general, the extension of such three-phase interface (the depth from the surface of noble metal catalyst) tends to vary according to such changes in the atmospheric temperature, viscosity of electrolysis solution, etc.

With the gold supported carbon manufactured by the above-described technique, the particle size of gold particle is greater than the particle size of carbon, so coagulation in water solution readily occurs. For this reason, it was difficult to cause gold particles to be dispersed uniformly. If the gold supported carbon produced with such non-uniform gold particles is employed as noble metal catalyst, there will occur conspicuous change in the extension of the three-phase interface (the depth from the surface of noble metal catalyst) when change occurs in the atmospheric temperature, viscosity of electrolysis solution, etc. And, such change in the extension of three-phase interface would often provide such effect as irregularity in the gas detection performance for instance.

Therefore, the object of the present invention is to provide a controlled potential electrolysis gas sensor having less possibility of gas detection performance irregularity through stabilization of the extension of three-phase interface.

Solution

For accomplishing the above-noted object, according to the present invention, in a controlled potential electrolysis gas sensor including, as gas electrodes for detecting gas, a working electrode for electrochemically reacting gas to be detected, a counter electrode with respect to the working electrode, and a reference electrode for controlling potential of the working electrode, the gas electrodes being disposed to face an electrolysis solution accommodating portion of an electrolysis tank accommodating electrolytic solution;

according to a first characterizing feature, each electrode includes a noble metal catalyst layer; and on the noble metal catalyst layer of at least one of the working electrode and the reference electrode, there is formed a polymer layer having ion conductivity and water permeability.

With the above-described configuration, since a polymer layer having ion conductivity and water permeability is formed on the noble metal catalyst layer of the working electrode alone or of the reference electrode alone, or on the noble metal catalyst layers of the working electrode and the reference electrode, it is possible to avoid direct contact between the electrolysis solution and the noble metal catalyst layer. And, as this polymer layer has ion conductivity and water permeability, $H^+$ ions and $H_2O$ molecules can move from the electrolysis solution side to the noble metal catalyst layer side via this polymer layer. That is, the three-phase interface as the field of electrode reaction in the controlled potential electrolysis gas sensor will be present in the vicinity of the boundary between the noble metal catalyst layer and the polymer layer.

Therefore, with the above-described configuration, it is possible to avoid direct contact between the electrolysis solution and the noble metal catalyst layer and also to cause the three-phase interface to be present in the vicinity of the boundary between the noble metal catalyst layer and the polymer layer. Consequently, even in the event of change in the atmospheric temperature, the viscosity of the electrolysis solution, etc., this change will hardly lead to change in the forming extension of the three-phase interface.

Thus, due to formation of the polymer layer on the noble metal catalyst layer, it is possible to stabilize the forming extension of the three-phase interface, so that irregularity will occur less likely in the gas detection performance of the controlled potential electrolysis gas sensor.

Especially, if the polymer layer is formed in the working electrode, it becomes possible to stabilize the sensitivity against temperature and moisture variations. Whereas, if the polymer layer is formed in the reference electrode, it becomes possible to suppress sharp noise generation.

According to a second characterizing feature of the controlled potential electrolysis gas sensor relating to the present invention, there is formed a penetration region where a portion of the polymer layer penetrates to the surface of the noble metal catalyst layer.

With the above-described configuration, the penetration region is provided as a region in which the polymer of the polymer layer and the noble metal catalyst of the noble metal catalyst layer are present in a mixed state. With formation of such region where the two components are present in a mixed state, it is possible to form the polymer layer on the noble metal catalyst layer in a reliable manner without any gaps relative thereto. Consequently, intrusion of electrolysis solution to such gaps can be avoided, thus irregularity in the gas detection performance will occur even less likely.

According a third characterizing feature of the controlled potential electrolysis gas sensor relating to the present invention, the penetration region is formed in the vicinity of the boundary between the noble metal catalyst layer and the polymer layer.

With the above-described configuration, the penetration region can form a part of the three-phase interface as the field of electrode reaction.

According a fourth characterizing feature of the controlled potential electrolysis gas sensor relating to the present invention, the polymer layer is formed on the noble metal catalyst layer of each every electrode.

With the above-described configuration, the polymer layer can be formed on the noble metal catalyst layer of each and every electrode consisting of the working electrode, the counter electrode and the reference electrode. In the case of the controlled potential electrolysis gas sensor, e.g. the counter electrode and the reference electrode are sometimes formed on a single gas permeable membrane. In such case, the polymer layers can be formed at one time on the noble metal catalyst layers of the counter electrode and on the noble metal catalyst layers of the reference electrode respectively. Thus, efficient manufacture is made possible.

EMBODIMENTS

Next, embodiments of the present invention will be explained with reference to the accompanying drawings.

Figure 1:
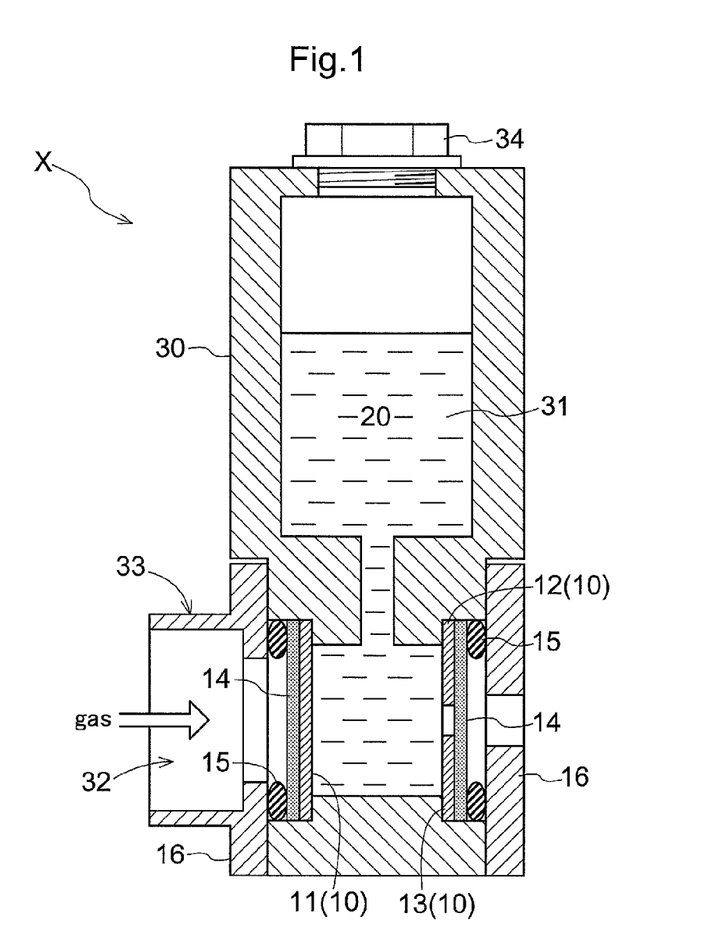
FIG. 1 is a section view showing a controlled potential electrolysis gas sensor according to the present invention.

As shown in FIG. 1, a controlled potential electrolysis gas sensor X includes, as gas electrodes for detecting gas, a working electrode 11 for electrochemically reacting gas to be detected ("detected gas" hereinafter), a counter electrode 12 with respect to the working electrode 11, and a reference electrode 13 for controlling potential of the working electrode 11, the electrodes 11, 12, 13 being disposed to face an electrolysis solution accommodating portion 31 of an electrolysis tank 30 accommodating electrolytic solution 20.

Each of the working electrode 11, the counter electrode 12 and the reference electrode 13 is formed by applying and sintering an amount of paste made of a known electrode material on a surface of a porous gas permeable membrane 14 having water repellant property. The working electrode 11, the counter electrode 12 and the reference electrode 13 are disposed to face each other.

The electrolysis tank 30 includes an opening portion 32 opened at a lateral portion thereof, thus forming a gas conducting portion 33. There are provided two gas permeable membranes 14. On one gas permeable membrane 14, the working electrode 11 is disposed; on the other gas permeable membrane 14, the counter electrode 12 and the reference electrode 13 are disposed. The gas permeable membrane 14 disposed on the side of the working electrode 11 is attached to the electrolysis tank 30 in such a manner to face the opening portion 32. The gas permeable membranes 14 can comprise any membranes having e.g. water repellency and gas-permeating property. For instance, a porous PTFE membrane having chemical resistance can be employed. The detected gas is introduced via the gas conducting portion 33 and reacts on the working electrode 11.

Each gas permeable membrane 14 and an O ring 15 are fixed by a lid member 16. In a bottom face of the electrolysis tank 30, there is formed an electrolysis inlet 34 for carrying out maintenance operation such as introduction of the electrolysis solution 20.

The above-described controlled potential electrolysis gas sensor X is connected to a gas detection circuit (not shown) having a current determining portion capable of detecting a current based on electrons generated on the working electrode 11 as result of the reaction of the detected gas and a potential controlling portion capable of controlling potential of the working electrode 11, thus being used as a gas detecting apparatus. The controlled potential electrolysis gas sensor X according to the present invention is utilized for detecting a hydrogen compound gas such as silane, phosphine, germane, arsine, diborane, etc.

Figure 3:
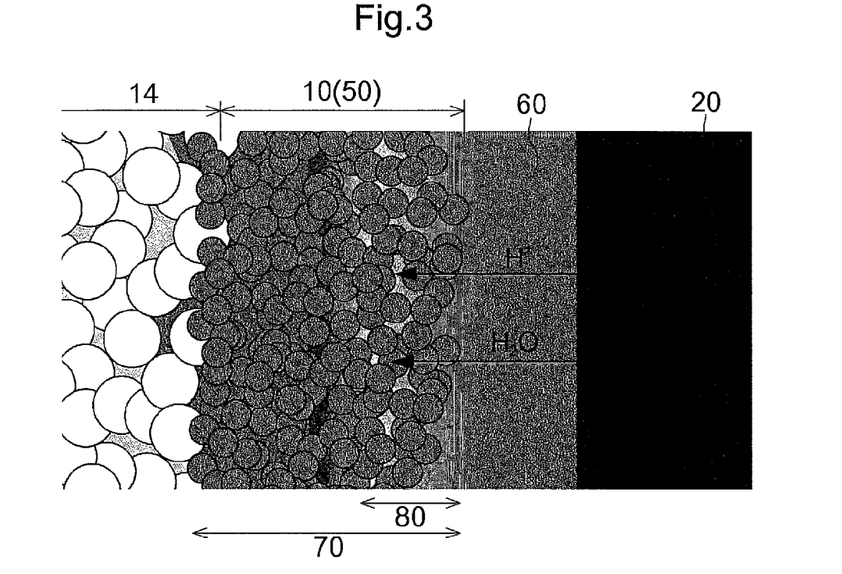
FIG. 3 is a section view showing a region of an electrode where a noble metal catalyst layer and a polymer layer are formed.

As shown in FIG. 3, each electrode 10 included in the controlled potential electrolysis gas sensor X of the present invention includes a noble metal catalyst layer 50. On the noble metal catalyst layer 50 of at least one of the working electrode 11 and the reference electrode 13, a polymer layer 60 having ion conductivity and water permeability is formed. In this configuration, such polymer layer 60 can be formed on the noble metal catalyst layer 50 of the working electrode 11 alone or the reference electrode 13 alone, or on the noble metal catalyst layers 50 of the working electrode 11 and the reference electrode 13.

This polymer layer 60 is not particularly limited as long as it has ion conductivity and water permeability. Such polymer layer 60 can be formed by e.g. applying a polymer comprising a sulfonic acid group introduced to perfluorocarbon-based main chain. Specifically, Nafion (registered trademark: manufactured by E.I. du Pont de Nemours and Company), Aciplex (registered trademark: manufactured by Asahi Kasei Corporation), Flemion (registered trademark: manufactured by Asahi Glass Co., Ltd.), etc. can be employed. For instance, Nafion has proton conductivity and water permeability and has also good acid resistance.

With formation of the polymer layer 60 having ion conductivity and water permeability on the noble metal catalyst layer 50 as provided in the above configuration, direct contact between the electrolysis solution 20 and the noble metal catalyst layer 50 can be avoided. The polymer layer 60 is formed by e.g. applying on the surface of the noble metal catalyst layer 50 by a known printing technique. In this, in the surface of the noble metal catalyst layer 50, a penetration region 80 can be formed where a portion of the polymer layer 60 penetrates to the surface of the noble metal catalyst layer 50. That is, this penetration region 80 is a region where the polymer of the polymer layer 60 and the noble metal catalyst of the noble metal catalyst layer 50 are present in a mixed state. With this formation of the region where the two component exist in a mixed state, it is possible to form the polymer layer 60 on/in the surface of the noble metal catalyst layer 50 in a reliable manner without forming any gaps relative thereto.

In the above, the penetration layer 80 is formed in the vicinity of the boundary between the noble metal catalyst layer 50 and the polymer layer 60. Namely, this penetration region 80 can form a part of a three-phase interface 70 as the field of electrode reaction.

Further, as the polymer layer 60 has ion conductivity and water permeability, $H^+$ ions and $H_2O$ molecules can move from the electrolysis solution 20 side to the noble metal catalyst layer 50 side via this polymer layer 60. That is, the three-phase interface 70 as the field of electrode reaction in the controlled potential electrolysis gas sensor X is present in the vicinity of the boundary between the noble metal catalyst layer 50 and the polymer layer 60.

Therefore, with the above-described configuration, it is possible to avoid direct contact between the electrolysis solution 20 and the noble metal catalyst layer 50 and also to cause the three-phase interface 70 to be present in the vicinity of the boundary between the noble metal catalyst layer 50 and the polymer layer 60. Consequently, even in the event of change in the atmospheric temperature, the viscosity of the electrolysis solution, etc., this change will hardly lead to change in the forming extension of the three-phase interface 70.

Thus, due to formation of the polymer layer 60 on the noble metal catalyst layer 50, it is possible to stabilize the forming extension of the three-phase interface 70, so that irregularity will occur less likely in the gas detection performance of the controlled potential electrolysis gas sensor X.

Especially, if the polymer layer 60 is formed in the working electrode 11, it becomes possible to stabilize the sensitivity against temperature and moisture variations. Whereas, if the polymer layer 60 is formed in the reference electrode 13, it becomes possible to suppress sharp noise generation. Also, the polymer layer 60 can be formed on the noble metal catalyst layer 50 of the counter electrode 12 as well. In this case, the polymer layers 60 can be formed on the noble metal catalyst layers 50 of all of the electrodes.

Figure 2:
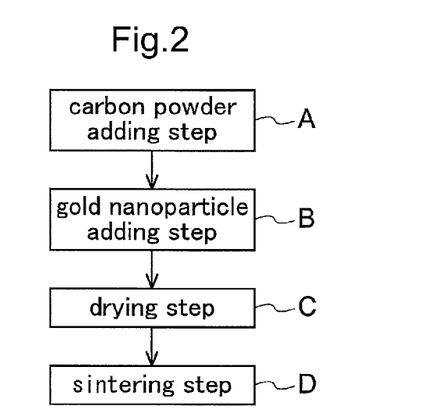
FIG. 2 is a flowchart schematically illustrating a process of manufacturing gold supported carbon.

As shown in FIG. 2, the noble metal catalyst is produced by carrying out a carbon powder adding step A for adding carbon powder and a surfactant to a solvent and stirring these together, a gold nanoparticle adding step B for adding colloidal solution in which gold nanoparticles are dispersed, a drying step C for drying the resultant mixture with keeping the temperature equal to or lower than the boiling point of the solvent, and a sintering step D for sintering the powder resulting from the drying at 250 to 400° C.

At the carbon powder adding step A, a predetermined amount of carbon powder is measured, to which the surfactant and water as the solvent are added and these are stirred well.

The carbon powder to be employed can be any known carbon powder, e.g. carbon black (particle size ranging from 5 to 300 nm). Acetylene black obtained by thermal decomposition of acetylene gas is preferred, but it is not limited thereto.

The surfactant can be any surfactant based on anion, cation, non-ion, betaine, etc.

At the gold nanoparticle adding step B, colloidal dispersion with gold nanoparticle dispersed therein is added to the solution obtained from the carbon powder adding step A.

The colloidal solution containing gold nanoparticles dispersed therein is under a state wherein gold particles having the above-described particle size are dispersed therein. To this colloidal solution, an additive such as a protecting agent can be added if necessary.

The gold colloidal solution can be prepared e.g. through utilization of intra-solution reduction reaction in which a citrate as a reducing agent is added to a gold chloride solution of e.g. tetrachloroaurate (III) and then the resultant mixture is heated to reduce the metal ions, thus forming colloids. However, the method is not limited thereto. In this method, by increasing/decreasing the addition amount of the reducing agent relative to gold chloride, the size of the gold colloidal particles can be varied. It is preferred that the gold nanoparticles have a particle size ranging from about 5 to 50 nm, but not limited to this range. In this case, a particle size distribution is preferably such that the ratio of particles ranging from 5 to 50 nm account for 90 wt % or more.

At the drying step C, the solution obtained from the gold nanoparticle adding step B are dried with keeping the temperature equal to or lower than the boiling point of the solvent (water). The temperature which is set equal to or lower than the boiling point of the solvent is not particularly limited. Yet, in case the solvent is water, the temperature should range from 80 to 100° C. As the method of drying, any method such as reduced pressure drying, vacuum drying, suction drying, hot air drying, etc. can be employed. Drying conditions used in these drying methods can be the known conditions.

At the sintering step D, the powder obtained from drying is sintered at from 250 to 450° C.

The sintering temperature employed in this embodiment is set to a temperature range at which progress of oxidization of carbon will occur under an air atmosphere and atmospheric pressure and evaporation of organic matter such as the surfactant employed will occur (250 to 450° C.).

The sintering period (duration) can be set to an appropriate period in which the surfactant, the colloid protecting agent, etc. will disappear completely through evaporation, sublimation, thermal decomposition. Therefore, depending on the amount of powder to be sintered, the sintering period can be reduced or extended. However, in consideration to particle growth of the gold nanoparticles or reduction in the activity due to sintering, the upper limit of the sintering period can be set to about 3 hours for instance. Further alternatively, it may be arranged such that the sintering step D is terminated upon arrival at a predetermined temperature, rather than setting some sintering period.

With the above-described technique, it is possible to produce gold supported carbon supporting gold nanoparticles dispersed therein. That is, the controlled potential electrolysis gas sensor X of the present invention can use gold supported carbon supporting gold nanoparticles dispersed therein, as the noble metal catalyst.

Further, in the gold supported carbon produced by the above-described method, the gold nanoparticles can be dispersed with particle size ranging from about 5 to 50 nm.

EXAMPLES

Example 1

With using the controlled potential electrolysis gas sensor X of the present invention, study was made as to how its zero point indication will vary according to atmospheric temperature variation (0 to 40° C.). As a comparison example, such change in the zero point indication was studied with using the conventional controlled potential electrolysis gas sensor having no polymer layer 60 formed therein. In each of these studies, two samples of the controlled potential electrolysis gas sensor were used. The respective results are shown in FIG. 4 and FIG. 5.

Figure 4:
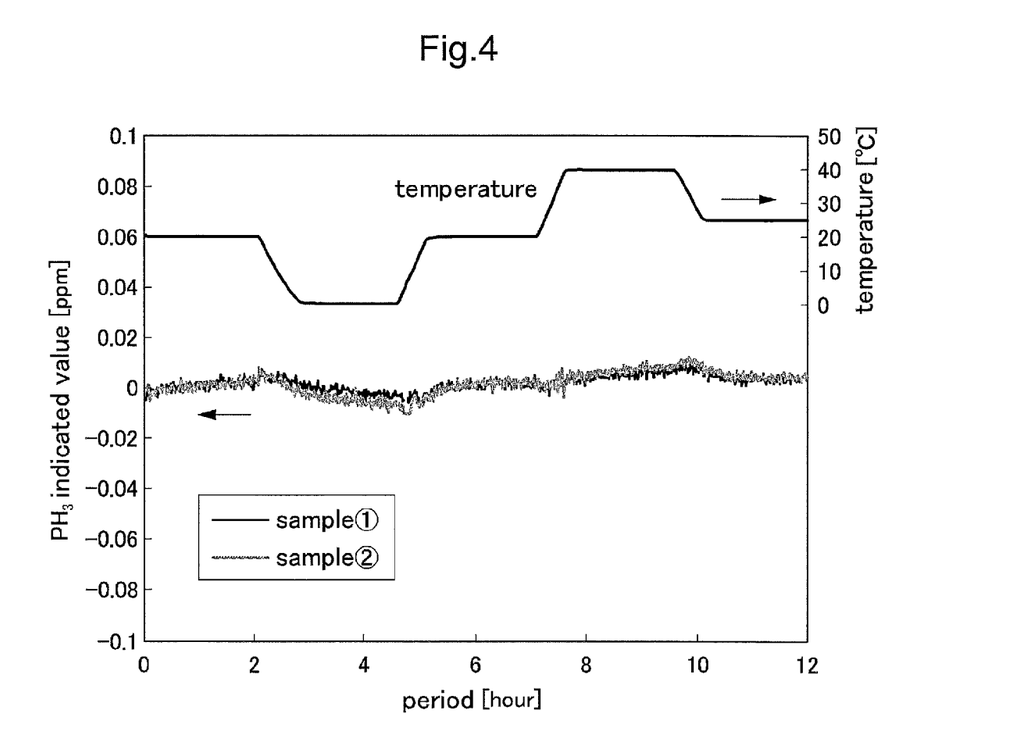
FIG. 4 is a graph showing result of study of variation in a zero point indication by the controlled potential electrolysis gas sensor according to the present invention.
Figure 5:
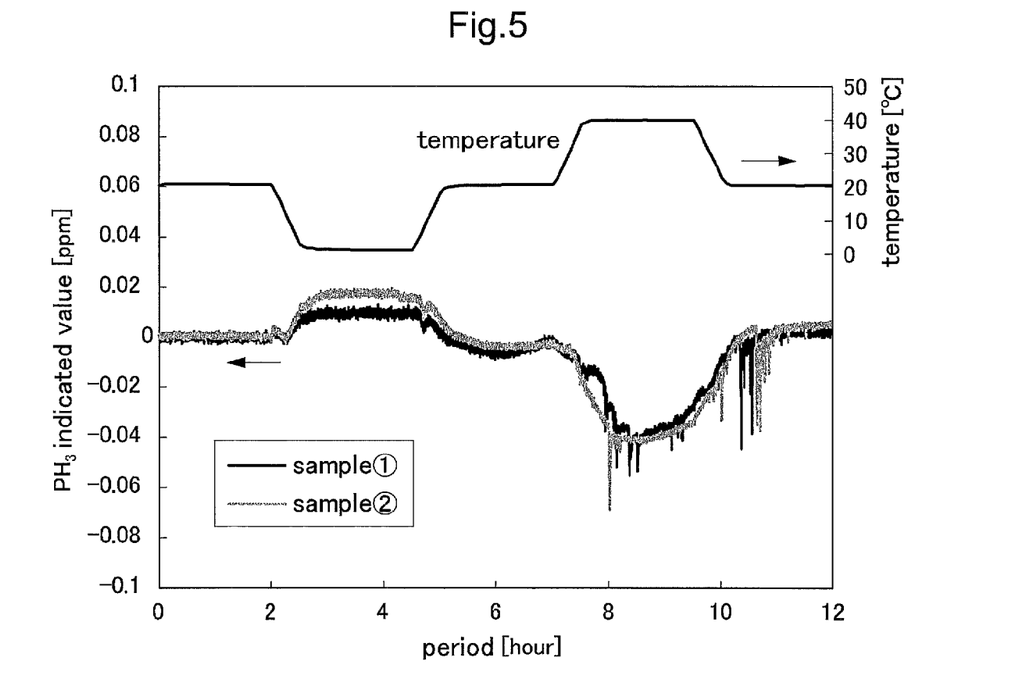
FIG. 5 is a graph showing result of study of variation in a zero point indication by a controlled potential electrolysis gas sensor according to the prior art.

As a result, in the case of the controlled potential electrolysis gas sensor X of the present invention, almost no change in the zero point indication was observed in the event of temperature variation (FIG. 4). Therefore, it was recognized that the controlled potential electrolysis gas sensor X of the present invention hardly suffers irregularity in its gas detection performance. On the other hand, in the case of the conventional controlled potential electrolysis gas sensor, changes in the zero point indication occurred in the case of low temperature near 0° C. as well as in the case of high temperature near 40° C. (FIG. 5).

Example 2

Figure 6:
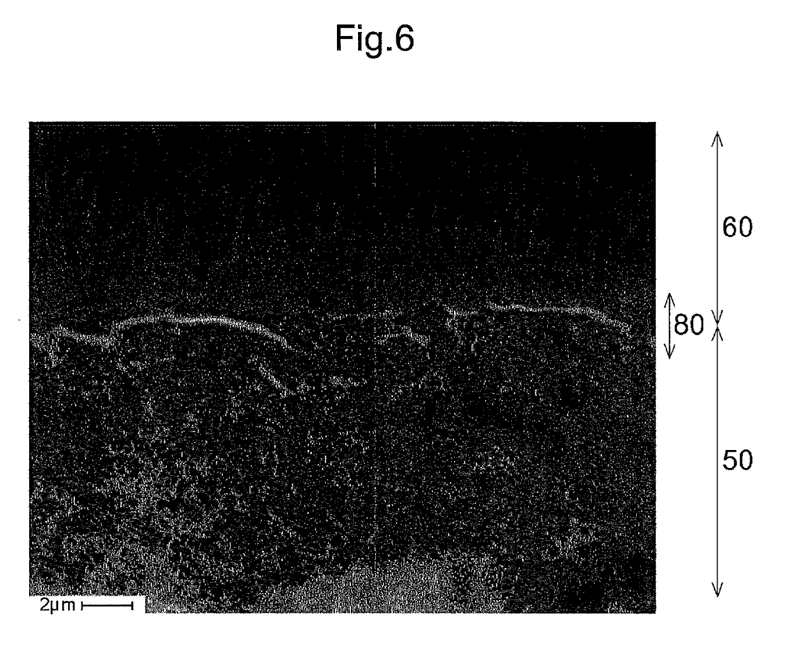
FIG. 6 is a photographic view showing a region of an electrode where a noble metal catalyst layer and a polymer layer are formed.
Figure 7A:
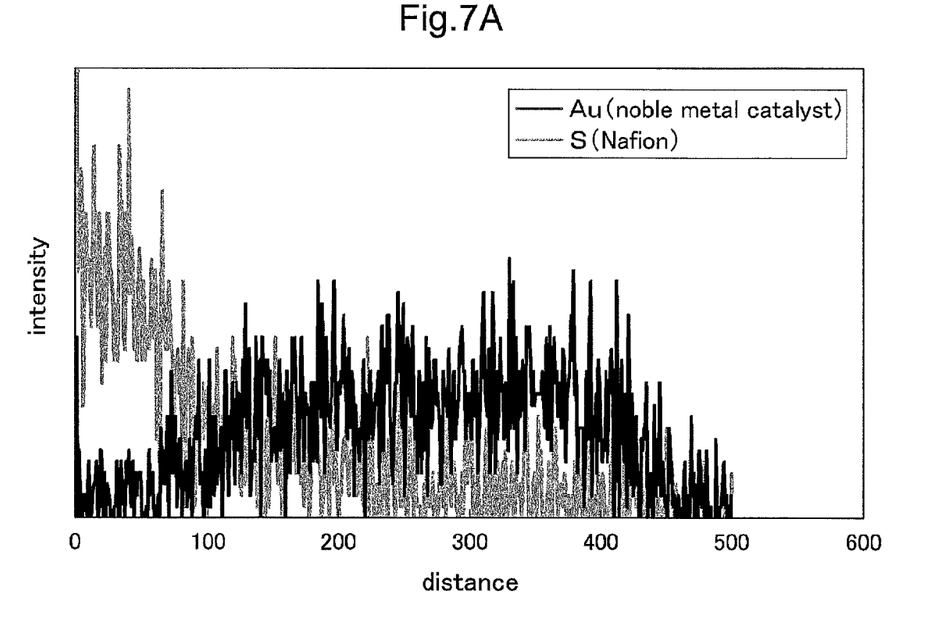
FIG. 7A is a graph showing result of element analysis of a noble metal catalyst layer, a polymer layer and a penetration region in case the polymer layer is formed by a printing technique.

With using the controlled potential electrolysis gas sensor X of the present invention, study was made with respect to the penetration region 80 formed adjacent the boundary between the noble metal catalyst layer 50 and the polymer layer 60 (Nafion). This penetration region 80 can be formed by applying an amount of Nafion resin to the surface of the noble metal catalyst layer 50 to form the polymer layer 60 by the printing technique.

Figure 7B:
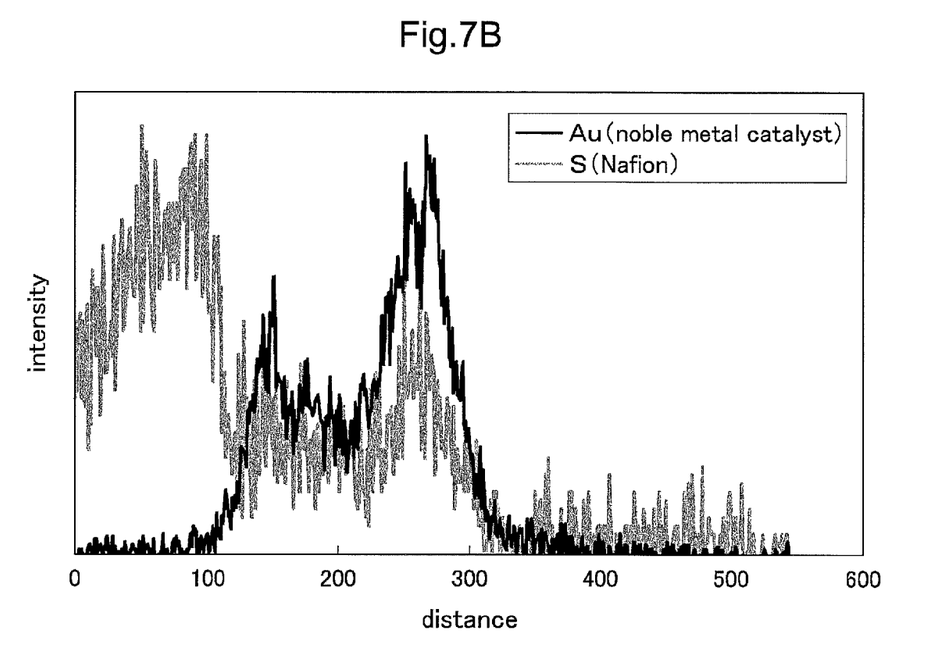
FIG. 7B is a graph showing result of element analysis of a noble metal catalyst layer, a polymer layer and a penetration region in case the polymer layer is formed by a spraying technique.

FIG. 6 is a photographic view showing section of the region where the noble metal catalyst layer 50 and the polymer layer 60 are formed in an electrode. FIG. 7A is a graph showing result of element analysis of a noble metal catalyst layer 50, a polymer layer 60 and a penetration region 80 in case the polymer layer 60 is formed by the printing technique. FIG. 7B is a graph showing result of element analysis of a noble metal catalyst layer 50, a polymer layer 60 and a penetration region 80 in case the polymer layer 60 is formed by spraying the Nafion resin on the surface of the noble metal catalyst layer 50, as a comparison example. FIGS. 7A and 7B show the results of the constituent element analyses carried out along the direction from a specified position (depth) of the formed polymer layer 60 toward the deep layer (toward the noble metal catalyst layer 50 side). Namely, the horizontal axis of each graph represents the depths from the specified position (depth) as relative distances.

Incidentally, the constituent elements of the noble metal catalyst layer 50 are H, Au, C, F; whereas, the constituents elements of Nafion are H, C, S, F. Therefore, presence of the noble metal catalyst layer 50 and the polymer layer 60 (Nafion) can be confirmed by detecting Au and S which respectively is contained only in either one of the above.

As a result, in FIG. 7A (printing technique), at the depth ranging from 0 to 50, the noble metal catalyst layer 50 and the polymer layer 60 (Nafion) were not present in a mixed state, thus it is recognized that no penetration region 80 was formed therein. On the other hand, it was recognized that at the depth ranging from 50 to 150 approximately in FIG. 7A, co-existence of Au of the noble metal catalyst layer 50 and S (Nafion) of the polymer layer 60 occurred, so this depth forms the penetration region 80.

Further, in FIG. 7B (spraying technique), at the depth ranging from 0 to 120, the noble metal catalyst layer 50 and the polymer layer 60 (Nafion) were not present in a mixed state, thus it is recognized that no penetration region 80 was formed therein. On the other hand, it was recognized that at the depth ranging from 120 to 300 approximately in FIG. 7B, co-existence of Au of the noble metal catalyst layer 50 and S (Nafion) of the polymer layer 60 occurred, so this depth forms the penetration region 80. Based on the above, it was recognized that in the case of forming the polymer layer 60 by the spraying technique (FIG. 7B), as compared with the case of forming the polymer layer 60 by the printing technique (7A), a portion of the polymer layer 60 penetrated to a deeper layer of the noble metal catalyst layer 50.

Example 3

In the case of forming the polymer layer 60 by the above-described printing technique and the case of forming it by other technique, how the zero point stability and response waveform varied was studied.

Figure 8A:
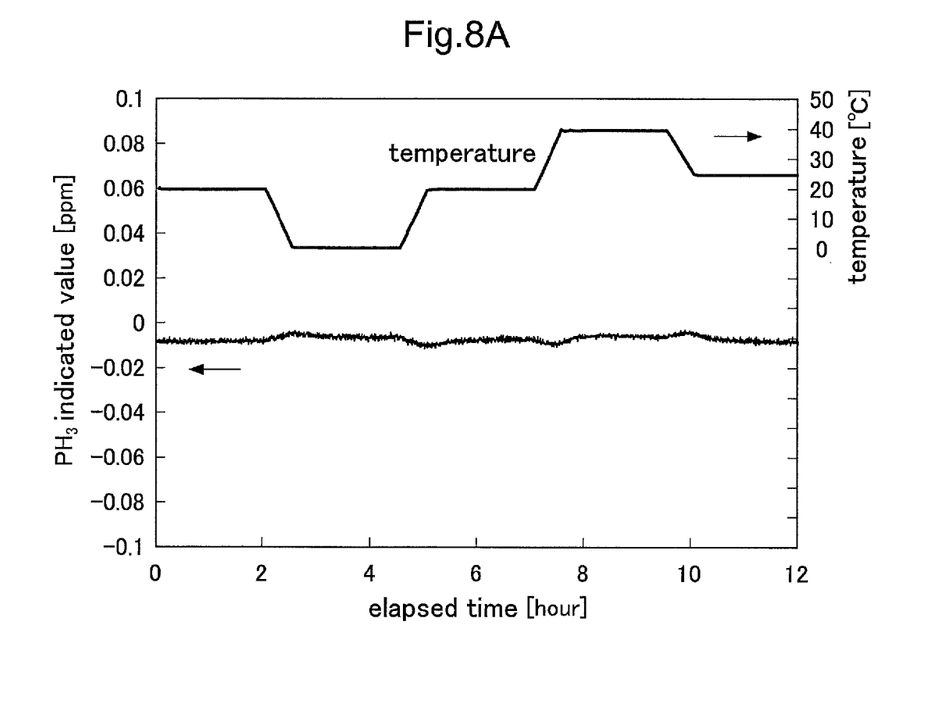
FIG. 8A is a graph showing result of study of zero point stability in case the polymer layer is formed by the printing technique.
Figure 8B:
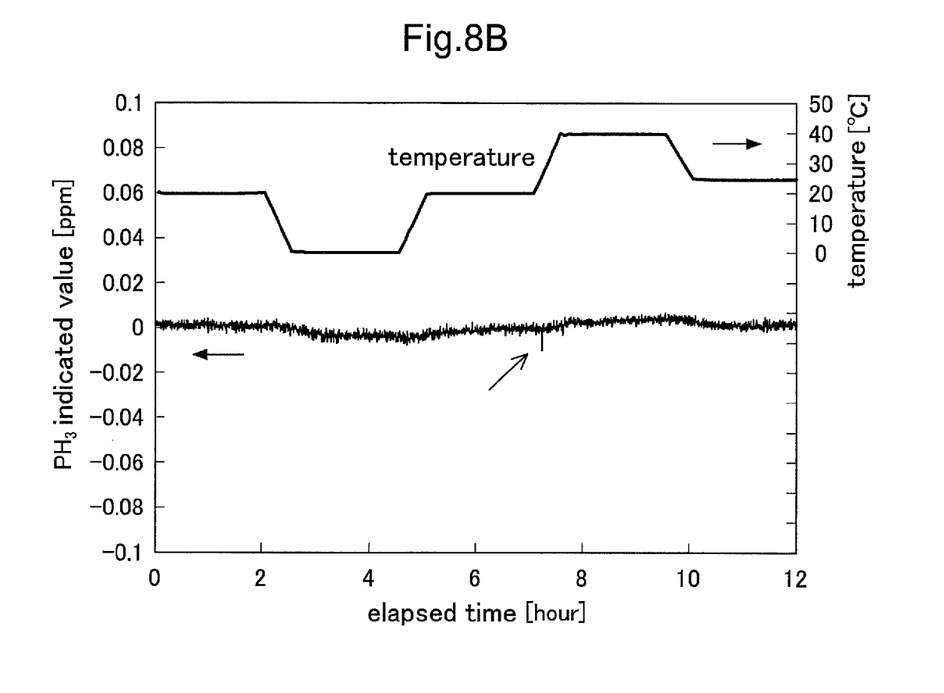
FIG. 8B is a graph showing result of study of zero point stability in case the polymer layer is formed by a normal temperature pressing technique.
Figure 8C:
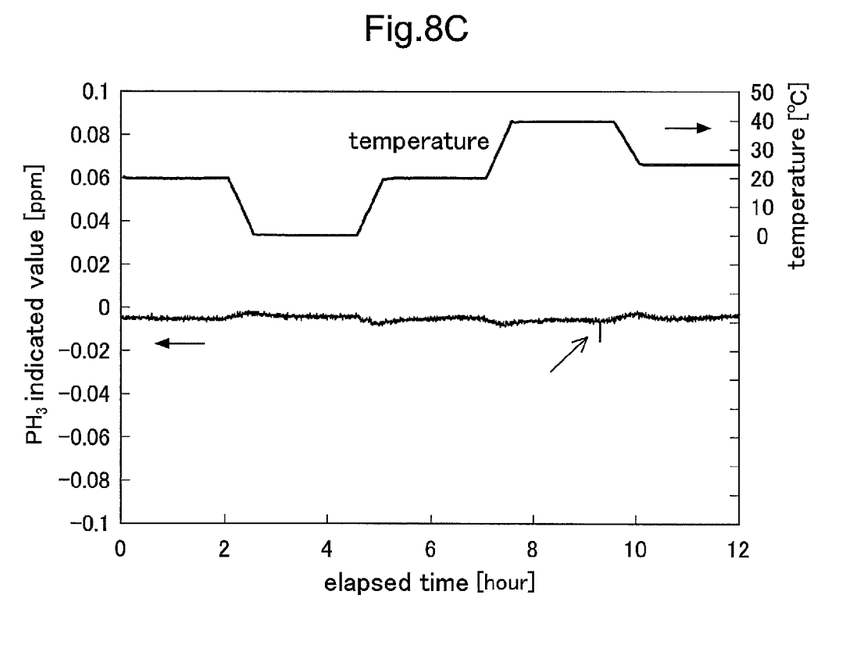
FIG. 8C is a graph showing result of study of zero point stability in case the polymer layer is formed by a heating pressing technique.

FIGS. 8A-8C show the results of study of the zero point stability.

FIG. 8A shows the result obtained in the case of forming the polymer layer 60 by the printing technique. In this case, the zero point indication was stable and no sudden change in the indication was recognized. This was believed to be attributable to the fact that the polymer layer 60 was formed on the surface of the noble metal catalyst layer 50 in a reliable manner without forming gaps relative thereto.

FIG. 8B shows the result obtained in the case of forming the polymer layer 60 on the surface of the noble metal catalyst layer 50 by the normal temperature pressing technique. In this case, sudden change in the indication was observed at about 20° C. near the lapsed period of 7 hours (the portion indicated by the arrow near the lapsed period of 7 hours in the drawing). This was believed to be attributable to the fact that such sudden change in the indication occurred due to accidental intrusion of the electrolysis solution to gaps which were formed inadvertently between the noble metal catalyst layer 50 and the polymer layer 60.

FIG. 8C shows the result obtained in the case of forming the polymer layer 60 on the surface of the noble metal catalyst layer 50 by the heating pressing technique (130° C.). In this case, sudden change in the indication was observed at about 40° C. near the lapsed period of 9 hours (the portion indicated by the arrow near the lapsed period of 9 hours in the drawing). This is probably because even with application of heat gaps were formed between the noble metal catalyst layer 50 and the polymer layer 60, which gaps allowed accidental intrusion of the electrolysis solution to gaps, thus resulting in such sudden change in the indication.

FIGS. 9A-9D show the results of the study of response waveforms.

Gas sensitivity was determined by exposure to 0.5 ppm of phosphine (base gas: atmospheric air) for 3 minutes.

Figure 9A:
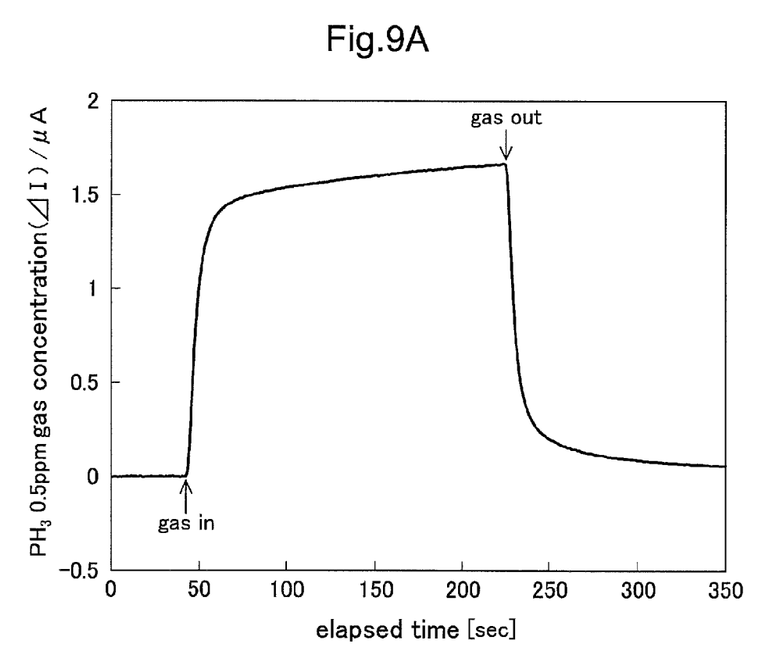
FIG. 9A is a graph showing result of study of response waveform in case the polymer layer is formed by the printing technique.

FIG. 9A shows the result obtained in the case of forming the polymer layer 60 by the printing technique. In this, high gas sensitivity (high response) was obtained immediately after the phosphine exposure. And, stable sensitivity was obtained thereafter also.

Figure 9B:
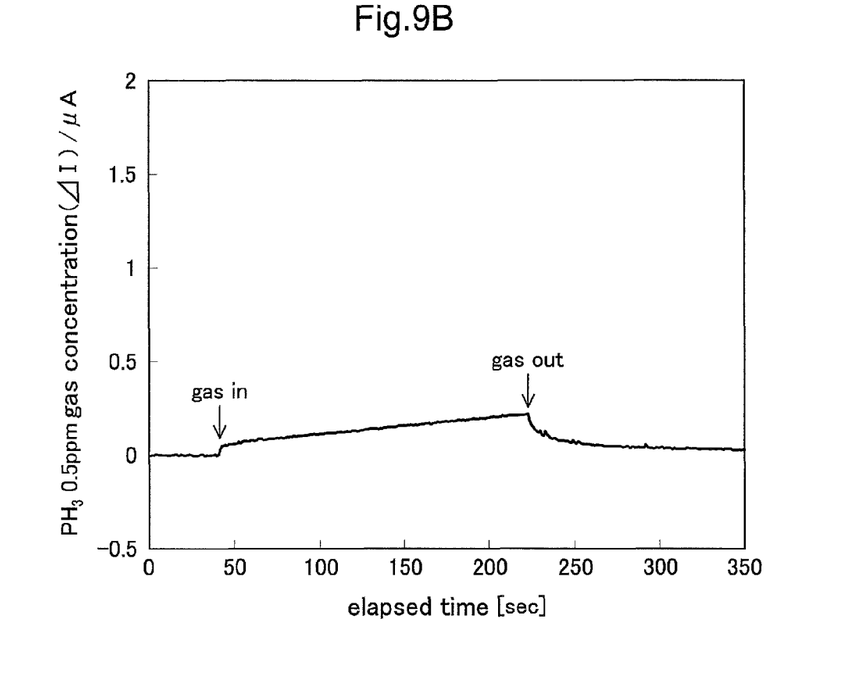
FIG. 9B is a graph showing result of study of response waveform in case the polymer layer is formed by the normal temperature pressing technique.

FIG. 9B shows the result obtained in the case of forming the polymer layer 60 on the surface of the noble metal catalyst layer 50 by the normal temperature pressing technique. In this, the obtained gas sensitivity was very low. This is probably because the three-phase interface formed by the noble metal catalyst layer 50 and the polymer layer 60 coming into contact with each other was much less than the three-phase interface formed by the printing technique.

Figure 9C:
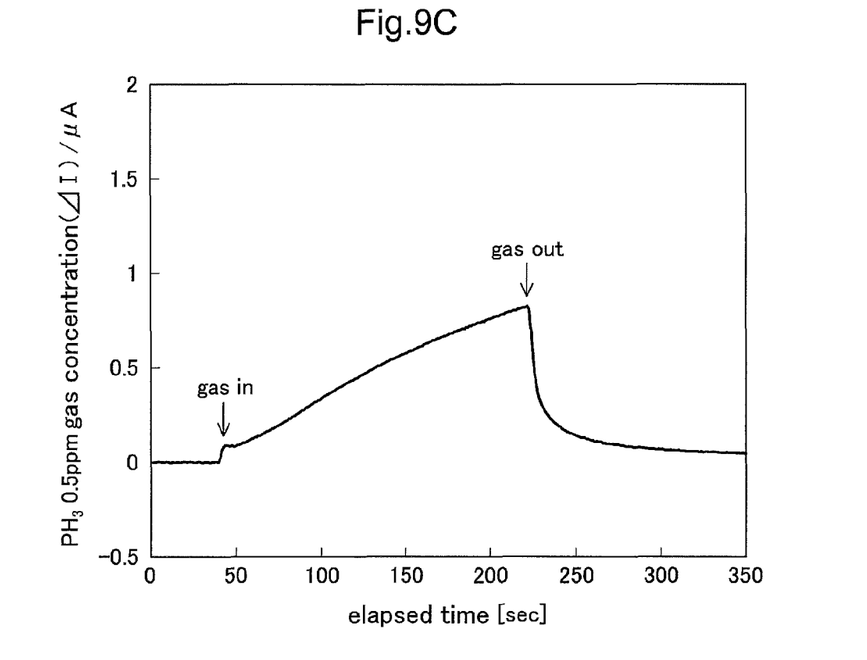
FIG. 9C is a graph showing result of study of response waveform in case the polymer layer is formed by the heating pressing technique.

FIG. 9C shows the result obtained in the case of forming the polymer layer 60 on the surface of the noble metal catalyst layer 50 by the heating pressing technique (130° C.). In this, the response was deemed low since it took a long time to obtain high gas sensitivity after the phosphine exposure. The probable reason for this is as follows. That is, with use of the heating pressing technique, the contacting portion between the noble metal catalyst layer 50 and the polymer layer 60 is more than that formed in the case of the normal temperature pressing technique. So, the gas sensitivity will improve, but heating pressing will result in collapsing of the noble metal catalyst layer 50, thus impairing gas diffusion performance, which led to the reduction in response.

Figure 9D:
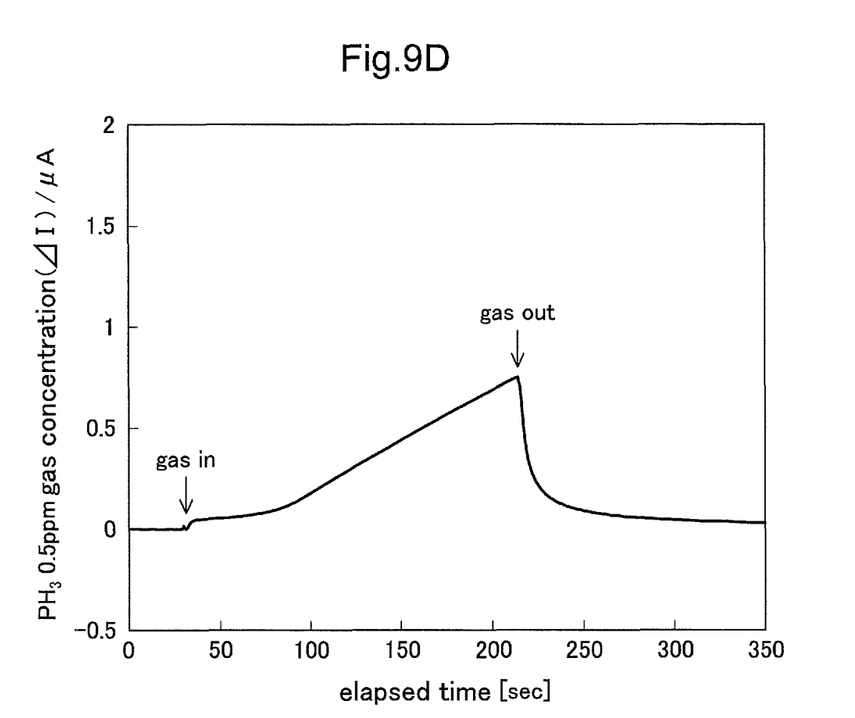
FIG. 9D is a graph showing result of study of response waveform in case the polymer layer is formed by the spraying technique.

FIG. 9D shows the result obtained in the case of forming the polymer layer 60 by applying the Nafion resin on the surface of the noble metal catalyst layer 50 by the spraying technique. In this, the response was deemed low since it took a long time to obtain high gas sensitivity after the phosphine exposure. The probable reason for this is as follows. That is, a portion of the polymer layer 60 penetrated to a deep layer of the noble metal catalyst layer 50, so the three-phase interface 70 as the field of electrode reaction extended to a deep layer of the noble metal catalyst layer 50, which led to the reduction in response.

Therefore, it was found that forming of the polymer layer 60 on the surface of the noble metal catalyst layer 50 should be carried out not by the spraying technique or the heating pressing technique, but by the printing technique.

INDUSTRIAL APPLICABILITY

The present invention is applicable to a controlled potential electrolysis gas sensor including, as gas electrodes for detecting gas, a working electrode for electrochemically reacting gas to be detected, a counter electrode with respect to the working electrode, and a reference electrode for controlling potential of the working electrode, the gas electrodes being disposed to face an electrolysis solution accommodating portion of an electrolysis tank accommodating electrolytic solution.

DESCRIPTION OF REFERENCE MARKS/NUMERALS

X controlled potential electrolysis gas sensor
11 working electrode
12 counter electrode
13 reference electrode
20 electrolysis solution
30 electrolysis tank
31 electrolysis solution accommodating portion
50 noble metal catalyst
60 polymer membrane
80 penetration region

The invention claimed is:
1. A controlled potential electrolysis gas sensor including, as gas electrodes for detecting gas, a working electrode for electrochemically reacting gas to be detected, a counter electrode with respect to the working electrode, and a reference electrode for controlling potential of the working electrode, the gas electrodes being disposed to face an electrolysis solution accommodating portion of an electrolysis tank accommodating electrolytic solution:
   wherein each electrode includes a noble metal catalyst layer;
   on the noble metal catalyst layer of at least one of the working electrode and the reference electrode, there is formed a polymer layer having ion conductivity and water permeability; and
   wherein the polymer layer is formed on the noble metal catalyst layer of each and every electrode.
2. The controlled potential electrolysis gas sensor according to claim 1, wherein the penetration region is formed in the vicinity of the boundary between the noble metal catalyst layer and the polymer layer.

3. The controlled potential electrolysis gas sensor according to claim 2, wherein the polymer layer is formed on the noble metal catalyst layer of each and every electrode.

4. The controlled potential electrolysis gas sensor according to claim 1,
wherein a penetration region is formed where a portion of the polymer layer penetrates to the surface of the noble metal catalyst layer; and,
wherein the penetration region is provided as a region in which polymer of the polymer layer and noble metal catalyst of the noble metal catalytic layer are present in a mixed state.

* * * * *